US00PP10436P

United States Patent [19]

Shaw

[11] Patent Number: Plant 10,436

[45] Date of Patent: Jun. 9, 1998

[54] STRAWBERRY PLANT NAMED 'PACIFIC'

[75] Inventor: Douglas V. Shaw, Davis, Calif.

[73] Assignee: The Regents of the University of California, Oakland, Calif.

[21] Appl. No.: 747,519

[22] Filed: Nov. 12, 1996

[51] Int. Cl.[6] ..... A01H 5/00

[52] U.S. Cl. ..... Plt./49

[58] Field of Search ..... Plt./49, 48

*Primary Examiner*—James R. Feyrer

*Attorney, Agent, or Firm*—Burns, Doane, Swecker & Mathis, L.L.P.

[57] ABSTRACT

'CN211' is a new and distinct cultivar of strawberry plant of the day-neutral type which has larger fruit and produces greater yields than 'Selva' or 'Seascape' when treated with appropriate planting regimes. Commercial appearance ratings for 'CN211' are superior to those for the comparison cultivars.

3 Drawing Sheets

FIELD OF THE INVENTION

This invention relates to a new and distinctive day-neutral type cultivar designated as 'CN211', which resulted from a cross performed in 1991 between 'Seascape' (U.S. Plant Pat. No. 7,614) and Cal 88.118-603. The cultivar is botanically identified as *F.×ananassa* Duch.

'CN211', was first fruited at the university of California Wolfskill Experimental Orchard, near Winters, Calif. in 1992, where it was selected, originally designated Cal 91.324-1, and propagated asexually by runners. Following selecting and during testing the plant of this disclosure was designated 'CN211'. With the decision that this plant was to be released, it was given the name 'Pacific' for the purposes of introduction into commerce and for international registration and recognition. Asexual propagules from this original source have been tested at the Wastonville Strawberry Research Facility, the South Coast Research and Extension Center, and to a limited extent in grower fields starting in 1994.

DETAILED DESCRIPTION OF THE INVENTION

Figure 1:
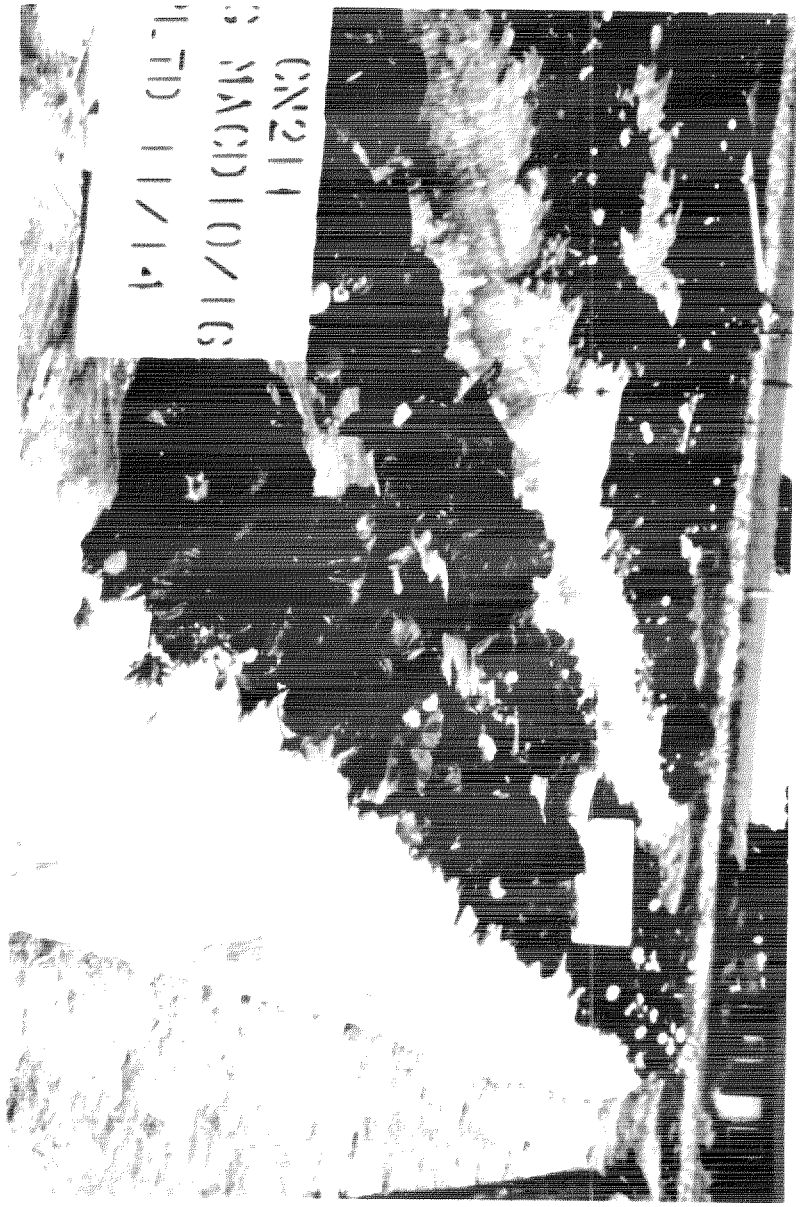
FIG. 1 depicts the general flowering and fruiting characteristics of the plant.
Figure 2:
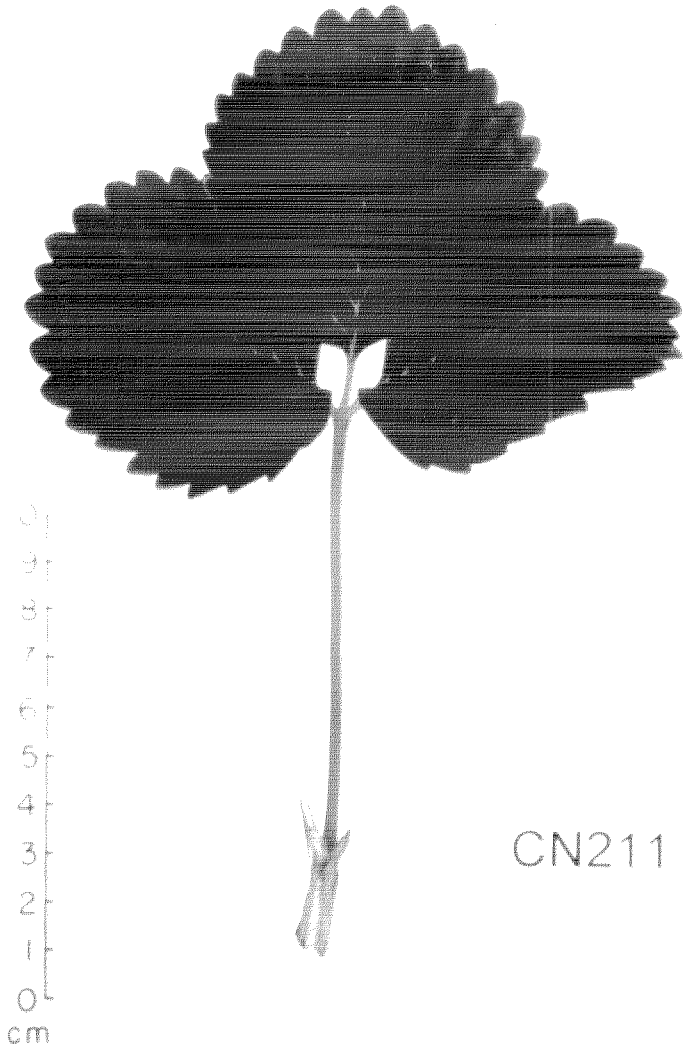
FIG. 2 depicts the typical mature leaf during late spring.
Figure 3:
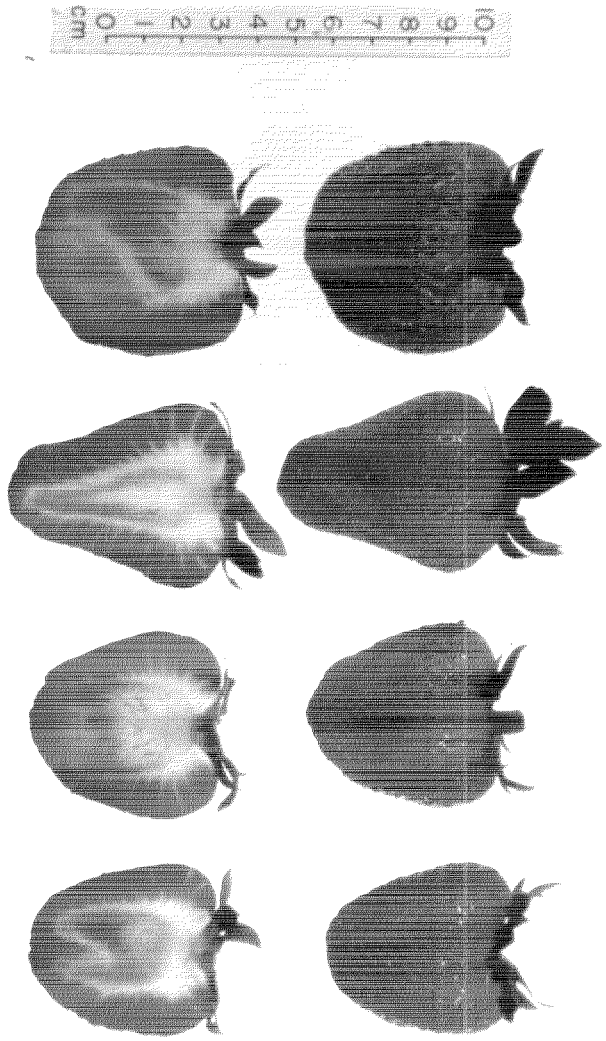
FIG. 3 depicts representative mid-season fruit.

'CN211' is moderate in expressing the day-neutral character, being a stronger day-neutral than 'Seascape', comparable to 'Selva' (U.S. Plant Pat. No. 5,266), and less so than 'Fern' (U.S. Plant Pat. No. 5,267) or 'Irvine' (U.S. Plant Pat. No. 7,172). The production pattern for 'CN211', is similar to that for 'Selva' and will be of special interest for winter plantings, where 'Selva' and 'Seascape' have been successful and summer plantings where 'Seascape' has been successful.

Plants and Foliage

Fruiting plants of 'CN211' are slightly more erect and perhaps slightly more vigorous than plants of 'Selva', less erect and less vigorous than plants of 'Seascape'. With appropriate treatment, 'CN211', has a similar sized plant to 'Selva', but is smaller in size than 'Seascape'. Comparative statistics for foliar characters near mid-season are given for the three cultivars in Table 1. Leaflets of 'CN211' are similar in size but considerably more rounded than leaves of 'Selva' or 'Seascape'. Leaves including petioles are somewhat longer but similar in width to the comparision cultivars. Petioles are thicker and more stiff than those of 'Selva' and are similar to those of 'Seascape'. 'CN211' has variable leaf convexity, generally flat or convex but not as convex as 'Selva', and has more and more pointed serrations than the comparison cultivars. The adaxial (upper) leaf surface for 'CN211' is lighter than for 'Seascape' but darker than 'Selva', whereas the abaxial surface is slightly lighter than either cultivar (Table 2).

Isozymes in Leaf Extracts

'CN211', has been classified for three isozyme systems using starch gel electrophoresis (Table 3): Phosopholucoisomerase (PGI), Leucine Aminopeptidase (LAP), and Phosphoglucomutase (PGM). It is distinguishable from both 'Selva' and 'Seascape' using this methodology. For electrophoretic procedures see: J. Amer. Soc. Hort. Sci. 106:684–687.

Disease and Pest Reaction

'CN211' is moderately susceptible to common leaf spot (*Ramularia tulasnei*), Anthracnose crown rot (*Colletotrichum acutatum*), and Verticillium wilt (*Verticillium dahliae*), and is relatively resistant to powdery mildew (*Sphaerotheca macularis*). When treated properly, it has tolerance to two-spotted spidermites (*Tetranychus urticae*) similar to or greater than 'Seascape' and 'Selva'. 'CN211', is tolerant to strawberry viruses encountered in California.

TABLE 1

Foliar characteristics for 'CN211', 'Selva', and 'Seascape'.

| Foliar Character | Cultivar 'Selva' | 'Seascape' | 'CN211' |
|---|---|---|---|
| Mid-tier leaflet Length (mm) | | | |
| mean | 72.6 | 72.8 | 73.1 |
| range | 65–88 | 65–82 | 67–81 |
| Width (mm) | | | |
| mean | 68.2 | 64.5 | 76.5 |
| range | 51–84 | 48–78 | 68–88 |

TABLE 1-continued

Foliar characteristics for 'CN211', 'Selva', and 'Seascape'.

| Foliar Character | Cultivar 'Selva' | 'Seascape' | 'CN211' |
|---|---|---|---|
| Mid-tier leaf | | | |
| Length (mm) | | | |
| mean | 119.2 | 123.8 | 131.7 |
| range | 94–139 | 80–155 | 118–148 |
| Width (mm) | | | |
| mean | 130.1 | 127.1 | 136.6 |
| range | 111–170 | 108–150 | 121–173 |
| # leaflets/leaf | 3 | 3, rarely 4 | 3 |
| Leaf convexity | mostly flat to convex | concave to convex, mostly flat to convex | flat to convex, few concave |
| Serrations | | | |
| number | few-moderate | moderate | moderate to many |
| shape | round to semi-pointed | semi-round to semi-pointed | semi-pointed |
| Leaf pubescence | moderate | moderate | moderate |
| Petiole pubescence | | | |
| density | heavy | mod. to heavy | mod. to heavy |
| direction | perpendicular | perpendicular to slight acropetal | perpendicular to basipetal |

Flowering, Fruiting, Fruit, and Production

Characteristics '*CN*211' is similar to other California day-neutral cultivars (e. g. 'Selva' and 'Seascape') in that it will flower independently of day length, given appropriate temperatrure and fertility conditions. Comparative statistics for flower and fruit characters near mid-season are given for the three cultivars in Table 4. The primary flowers for 'CN211' are similar in size, perhaps slightly large than 'Selva' and 'Seascape'; the sepals are somewhat larger than for 'Seascape' and substantially larger than for 'Selva'. The calyx for 'CN211' varies from slightly indented to slightly necked, and each primary flower has 5–7 petals. The fruit shape for 'CN211' can vary but is typically a short symmetric conic, and is easily distinguished from other California day-neutral cultivars. External fruit color for 'CN211' is darker than for 'Selva' and lighter than for 'Seascape', and fruit is substantially more glossy than either comparison cultivar. Internal color for 'CN211' is similar to that for 'Selva' and lighter than that of 'Seascape'. Achenes vary but are red to dark red, and are even with the fruit surface or slightly extruded.

'CN211' has been tested under a variety of cultural regimes, and optimal performance is obtained when nursery treatments and nutritional programs similar to those for 'Selva' and 'Seascape' are used. In general, 'CN211' is very similar in plant vigor to 'Selva' and requires similar chilling to insure fruit quality and tolerance to spidermites.

When treated with appropriate planting regimes, 'CN211' has larger fruit and produces greater yields than 'Selva' or 'Seascape' (Table 5). Production for 'CN211' initiates slightly earlier than the comparison cultivars and it produces slightly larger quantities of late-season fruit. Commercial appearance ratings have been superior to those for the comparison cultivars. Fruit firmness is similar to that for 'Selva' and greater than that for 'Seascape'. Subjectively, 'CN211' has very good flavor, substantially better than 'Selva', and equal to that for 'Seascape'. The fruit will be outstanding for both fresh market and processing, and will be useful for home garden purposes.

TABLE 2

Foliar and fruit color characteristics for 'CN211', 'Selva', and 'Seascape'.

| Color Character | Cultivar 'Selva' | 'Seascape' | 'CN211' |
|---|---|---|---|
| Leaf color (CIELAB) | | | |
| Adaxial | | | |
| L* | | | |
| mean | 31.9 | 29.1 | 30.8 |
| range | 30.2–33.7 | 26.9–32.3 | 28.2–33.4 |
| a* | | | |
| mean | −6.5 | −5.1 | −7.2 |
| range | −5.7—7.2 | −2.4—6.6 | −5.6—9.1 |
| b* | | | |
| mean | 12.7 | 11.3 | 13.5 |
| range | 9.8–15.8 | 9.5–16.5 | 8.7–19.2 |
| Munsell | 2.5G 3/3 | 2.5GY 4/3 | 2.5GY 5/5 |
| Abaxial | | | |
| L* | | | |
| mean | 48.3 | 48.3 | 50.5 |
| range | 47.2–50.4 | 47.0–49.6 | 49.1–52.0 |
| a* | | | |
| mean | −7.7 | −7.2 | −8.0 |
| range | −7.3—8.3 | −6.3—8.0 | −7.6—8.3 |
| b* | | | |
| mean | 17.9 | 18.1 | 16.7 |
| range | 16.7–19.4 | 16.7–19.0 | 15.1–18.7 |
| Munsell | 7.5GY 4/4 | 10GY 4/5 | 10Y 5/5 |
| L* | | | |
| mean | 28.5 | 25.4 | 27.3 |
| range | 23.7–33.1 | 22.7–31.5 | 25.8–29.6 |
| a* | | | |
| mean | 29.7 | 28.7 | 29.8 |
| range | 26.9–31.5 | 25.4–33.1 | 25.6–35.6 |
| b* | | | |
| mean | 16.9 | 13.7 | 15.3 |
| range | 14.4–22.1 | 9.3–19.8 | 12.4–19.5 |
| Munsell | 5R 4/12 | 5R 3/7<br>5R 4/12 | 5R 4/12 |
| Internal | | | |
| L* | | | |
| mean | 48.8 | 45.5 | 51.3 |
| range | 44.4–53.1 | 38.3–55.0 | 47.0–57.0 |
| a* | | | |
| mean | 35.2 | 37.8 | 34.0 |
| range | 31.5–39.5 | 30.8–42.7 | 26.3–41.2 |
| b* | | | |
| mean | 29.4 | 26.9 | 21.7 |
| range | 26.9–33.9 | 21.9–34.2 | 16.6–27.2 |
| Munsell | 5R 5/13 | 7R 5/13 | 5R 5/13 |

*CIELAB is the abbreviation of the international color system known as "Commission Internationale De L'Eclairage" 1978. Recommendations on uniform color spaces – color difference equations, psychometric color terms Supplement No. 2 to CIE Publication No. 15. PARIS.-

TABLE 3

Isozyme phenotypes for 'CN211', 'Selva', and 'Seascape'.

| | Cultivar | | |
|---|---|---|---|
| locus | 'Selva' | 'Seascape' | 'CN211' |
| PGI | A2 | A4 | A4 |
| LAP | B3 | B3 | B3 |
| PGM | C2 | C2 | C1 |

TABLE 4

Flowered fruit characters for 'CN211', 'Selva', and 'Seascape'.

| | Cultivar | | |
|---|---|---|---|
| Character | 'Selva' | 'Seascape' | 'CN211' |
| # petals | | | |
| mean | 5.8 | 6.1 | 5.6 |
| range | 5–8 | 5–7 | 5–7 |
| Flower position (relative to foliage) | even or interior | most even some interior or exposed | mostly even |
| Calyx diam. (mm) | | | |
| mean | 29.0 | 35.7 | 34.4 |
| range | 22–35 | 30–40 | 27–39 |
| Corolla diam. (mm) | | | |
| mean | 37.5 | 35.7 | 36.6 |
| range | 31–43 | 32–40 | 32–43 |
| Fruit shape length/width | | | |
| ratio | 1.16 | 1.15 | 1.05 |
| range | 10.2–1.25 | 1.00–1.31 | 1.00–1.28 |

TABLE 4-continued

Flowered fruit characters for 'CN211', 'Selva', and 'Seascape'.

| | Cultivar | | |
|---|---|---|---|
| Character | 'Selva' | 'Seascape' | 'CN211' |
| subjective | conic to flat conic | mostly sharp conic | sharp conic |
| Calyx position | even with shoulder | even/slight neck | slight neck to slight indent |
| Seed position | even/slight extrude | slight indent to slight extrude | even/slight extrude |

TABLE 5

Performance of 'CN211', 'Selva', and 'Seascape' evaluated at the Watsonville Research Facility in 1995 and 1996. All plants for these trials were harvested from Macdoel on October 16 or 17, and planted with four weeks supplemental storage prior to planting. Harvest was initiated in early April and continued through the first week of October. (52" 2-row beds, 17,300 plants/acre, 100 grams/plant = 316.3 crates/acre)

| Item | Yield (g/plant) | Late Yield (g/plant) | Appearance Score | Size (g/fruit) | Firmness |
|---|---|---|---|---|---|
| 'Selva' | 1,764 | 389 | 3.2 | 24.4 | 7.3 |
| 'Seascape' | 1,832 | 375 | 3.3 | 24.0 | 6.9 |
| 'CN211' | 1,740 | 307 | 3.5 | 27.1 | 7.7 |

Late yield includes harvest from August 20 through October 10.

I claim:

1. The new and distinct cultivar of strawberry plant substantially as herein described and illustrated.

* * * * *

CN211